| United States Patent [19] | [11] Patent Number: 4,760,164 |
| Park et al. | [45] Date of Patent: Jul. 26, 1988 |

[54] PROCESS FOR PRODUCING α-L-ASPARTYL-L-PHENYLALANINE METHYL ESTER

[75] Inventors: Jung Y. Park; Gug Y. Cheon, both of Seoul; Do Y. Ahn, Kyunggi-do; Dong J. Park, Seoul, all of Rep. of Korea

[73] Assignee: Korea Green Cross Corporation, Kyungki-Do, Rep. of Korea

[21] Appl. No.: 832,681

[22] Filed: Feb. 25, 1986

[51] Int. Cl.$^4$ .................... C07C 99/12; C07C 103/52
[52] U.S. Cl. ........................................ 560/40; 560/41; 426/548
[58] Field of Search .................. 260/998.21; 546/247; 426/548; 548/478; 549/477, 253; 560/38, 40, 41

[56] References Cited

U.S. PATENT DOCUMENTS 3,933,781  1/1976  Bachman et al. ............... 260/112.5
4,348,317  9/1982  Bachman ....................... 260/112.5 R Primary Examiner—Delbert R. Phillips
Assistant Examiner—Nathan M. Nutter
Attorney, Agent, or Firm—Birch, Stewart, Kolasch & Birch

[57] ABSTRACT

A process for preparing an α-L-aspartyl-L-phenylalanine methyl ester which comprises the steps of reacting formyl-L-aspartic anhydride with L-phenylalanine in the presence of water at a high pH, to produce formyl-α-L-aspartyl-L-phenylalanine; removing the formyl group from the formyl-α-L-aspartyl-L-phenylalanine and esterifying the resultant compound with methanol and hydrogen chloride to produce the hydrogen chloride salt of α-L-aspartyl-L-phenylalanine methyl ester; neutralizing the hydrogen chloride salt of α-L-aspartyl-L-phenylalanine methyl ester; and filtering the neutralized solution to produce α-L-aspartyl-L-phenylalanine methyl ester.

4 Claims, No Drawings

PROCESS FOR PRODUCING α-L-ASPARTYL-L-PHENYLALANINE METHYL ESTER

DETAILED EXPLANATION OF THE INVENTION

The present invention relates to a process for producing α-L-aspartyl-L-phenylalanine methyl ester. More particularly, the present invention pertains to a new and improved process for the preparation of α-L-aspartyl-L-phenylalanine methyl ester called "Aspartame" of the following formula (I) in high yield.

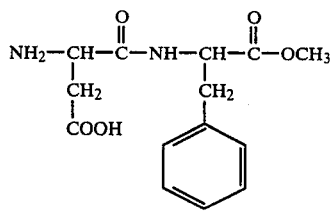

The compound of the present invention is useful because of its potent sweetening properties. The artificial sweetening agent of the present invention is utilized as a substitute for sugar in edible materials, which may be advantageously used by diabetics or others who desire to reduce their caloric intake. Various large scale methods for the preparation of α-L-aspartyl-L-phenylalanine methyl ester have been disclosed. The typical methods comprise the steps of: (a) protecting the amino group of aspartic acid with a proper protecting group; (b) dehydrating the protected compound to convert it into the corresponding anhydride; (c) condensing the anhydride with L-phenylalanine methyl ester; and (d) removing the protecting group.

Another method comprises the steps of: (a) condensing the anhydride with L-phenylalanine; (b) removing the protecting group for the amino group; and (c) esterifying the resulting compound with methanol.

Although there are several other methods for manufacturing the subject compound, almost all of them must use a large quantity of organic solvent and reagents and require complicated steps, such as fractional distillation or distillation under reduced pressure etc., for the removal or recovery of the organic solvents used. Furthermore, when N-protected-L-aspartic anhydride is reacted with L-phenylalanine methyl ester or L-phenylalanine, β-isomers of the product, which do not possess the sweetening property is produced as a byproduct. Thus, it is necessary to separate the β-isomers from the resulting mixture. As the result, the yield of the desired product is reduced and a large quantity of expensive L-phenylalanine is wasted.

When N-protected-L-aspartic anhydride is condensed with the esterified compound of L-phenylalanine, a large amount of β-isomers of the product are produced. In addition, during the separation of the protecting group from the N-protected-α-L-aspartyl-L-phenylalanine methyl ester, a large proportion of the methyl group is hydrolyzed. Furthermore, in order to use the process on an industrial scale, a large quantity of corrosive solvent should be separated and purified.

Another process which comprises the step of reacting the N-protected-L-aspartic anhydride directly with L-phenylalanine can avoid the disadvantages of hydrolysis of the methyl group during separation of the protecting group. Also, the process can reduce the quantity of by-product (β-isomer) in the condensation step of L-phenylalanine with N-protected-L-aspartic anhydride. However, the yield of the desired product in each step, namely, the condensation step of L-phenylalanine with N-protected-L-aspartic anhydride and the separation step of the N-protecting group and the esterification, has been low.

OBJECTS AND SUMMARY OF THE INVENTION

Accordingly, it is therefore an object of the present invention to provide a novel process for the production of α-L-aspartyl-L-phenylalanine methyl ester by coupling L-phenylalanine with N-protected-L-aspartic anhydride in high yield by utilizing a very small quantity of organic solvent and reagents.

Another object of the present invention is to provide an improved process for preparing α-L-aspartyl-L-phenylalanine methyl ester without the need for using complicated processes such as distillation, evaporation, etc., under reduced pressure.

Yet another object of the present invention is to provide an improved process for preparing α-L-aspartyl-L-phenylalanine methyl ester with a high purity of the β-isomer and without the production of a large quantity of the β-isomer.

A further object of the present invention is to provide a simple, economical process for the production of α-L-aspartyl-L-phenylalanine methyl ester which is suitable for industrial production.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention relates to an improved process for producing α-L-aspartyl-L-phenylalanine methyl ester in high yield by coupling L-phenylalanine with N-masked-L-aspartic anhydride.

DETAILED DESCRIPTION OF THE INVENTION

The present invention provides an economical process for the production of α-L-aspartyl-L-phenylalanine methyl ester of formula (I) which comprises the following steps of: (a) reacting formyl-L-aspartic anydride of formula (II) below, with L-phenylalanine in the presence of water at a high pH utilizing an autotitration apparatus to produce formyl-α-L-aspartyl-L-phenylalanine; (b) removing the formyl group from the formyl-α-L-aspartyl-L-phenylalanine and esterifying the resultant compound with methanol to produce hydrogen chloride salt of α-L-aspartyl-L-phenylalanine methyl ester; (c) neutralizing the hydrogen chloride salt of α-L-aspartyl-L-phenylalanine methyl ester; and (d) filtering the neutralizing solution of the hydrogen chloride salt of α-L-aspartyl-L-phenylalanine methyl ester.

The process of the present invention utilizes formyl-L-aspartic anhydride of formula (II) which is formylated and dehydrated by reacting L-aspartic acid with formic acid and acetic anhydride.

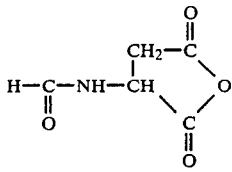

It has been found that a high purity, a high yield of the intermediate compound formyl-α-L-aspartyl-L-phenylalanine can be obtained by reacting formyl-L-aspartic anhydride of formula (II) with L-phenylalanine in the presence of water at high pH.

In general, it has been known that water or alcohols should be excluded from the reaction system in the condensation reaction of an anhydride of amino acids because the reaction rate of the anhydride with water or alcohols is very fast.

However, it has been found that, in the case of the reaction between these two compounds, advantageous results, such as a favorable α/β isomer ratio, can be obtained by utilizing water as the reaction medium, and the competing reactions such as hydrolysis and alcoholysis of formyl-L-aspartic anhydride can be controlled by lowering the reaction temperature. It has also been found that the yield of formyl-α-L-aspartyl-L-phenylalanine in such a reaction system is selectively very high. The preparation of the hydrogen chloride salt of α-L-aspartyl-L-phenylalanine methyl ester from the formyl-α-L-aspartyl-L-phenylalanine can be carried out by the following two methods:

(1) deformylating formyl-α-L-aspartyl-L-phenylalanine in the presence of hydrogen chloride, methanol and water. Then, adding methanol and hydrogen chloride directly to the resulting solution to obtain the chloride salt of α-L-aspartyl-L-phenylalanine methyl ester.

(2) deformylating formyl-α-L-aspartyl-L-phenylalanine in the presence of hydrogen chloride and water; and separating resultant α-L-aspartyl-L-phenylalanine. Then, esterifying the compound in the presence of hydrochloride, water and methanol to obtain the hydrogen chloride salt of α-L-aspartyl-L-phenylalanine methyl ester.

Furthermore, it has been found that the filtrate remaining after the separation of the hydrogen chloride salt of α-L-aspartyl-L-phenylalanine methyl ester can be utilized and enhances the production of the hydrogen chloride salt of α-L-aspartyl-L-phenylalanine methyl ester from α-L-aspartyl-L-phenylalanine in high yield. More particularly, a high yield of hydrogen chloride salt of α-L-aspartyl-L-phenylalanine methyl ester can be obtained by adding a suitable amount of hydrogen chloride and methanol to α-L-aspartyl-L-phenylalanine dissolved in the filtrate and agitating the resulting mixtures. It is believed that the by-product produced in the first esterification step restrains the formation of additional by-products and promotes the desired reaction to produce a more desired product in this chemical equilibrium reaction system.

The process of the present invention will now be explained in great detail. In the first step, to an aqueous slurry of L-phenylalanine (1 mole, 10~25% slurry), formyl-1-aspartic anhydride (0.5~2 mole) is added over a 1 hour period at a temperature of −5° C.~50° C. while adjusting the pH to about 6 to 13 utilizing an auto-titration apparatus. In this step, if the reaction temperature is high or the pH is too low, the formyl-1-aspartic anhydride is hydrolized and the desired condensation reaction is not properly accomplished. After the completion of the addition, the pH of the solution is adjusted to about 1 to 8 and a precipitate of formyl-α-L-aspartyl-L-phenylalanine is obtained. The yield of the formyl-α-L-aspartyl-L-phenylalanine on the basis of L-phenylalanine is usually above 80%. Advantageously, substantially no formyl-β-L-aspartyl-L-phenylalanine is produced. After filtration of the precipitate of formyl-α-L-aspartyl-L-phenylalanine, the remaining filtrate is collected. Additional precipitate of formyl-α-L-aspartyl-L-phenylalanine can be obtained by adjusting the pH of the filtrate utilizing concentrated hydrogen chloride.

In the second step, the formyl group is removed from the formyl-α-L-aspartyl-L-phenylalanine by heating at about 40 to 70° C. in dilute aqueous hydrogen chloride and formyl-α-L-aspartyl-L-phenylalanine is converted into α-L-aspartyl-L-phenylalanine. (Conversion rate: above 90%). By adjusting the pH of the resultant solution, α-L-aspartyl-L-phenylalanine is precipitated. After filtration of the precipitate, by again adjusting the pH of the remaining filtrate additional α-L-aspartyl-L-phenylalanine is obtained as a precipitate. The L-phenylalanine and L-aspartic acid can be recovered by hydrolysis of the remaining filtrate.

In the next step, the α-L-aspartyl-L-phenylalanine is dissolved in a mixture of water, hydrogen chloride and methanol and the reaction mixture is agitated. As the reaction goes on, hydrogen chloride salt of α-L-aspartyl-L-phenylalanine methyl ester is obtained as a crystallized precipitate. After filtration, the hydrogen chloride salt of α-L-aspartyl-L-phenylalanine methyl ester is neutralized and α-L-aspartyl-L-phenylalanine methyl ester is obtained as a final product. The filtrate from the filtration of hydrogen chloride salt of α-L-aspartyl-L-phenylalanine methyl ester is reused to produce the hydrogen chloride salt of α-L-aspartyl-L-phenylalanine methyl ester in high yield. The reaction is accomplished by the addition of hydrogen chloride, methanol and α-L-aspartyl-L-phenylalanine to the filtrate and subsequently stirring. The reaction is carried out at room temperature. The resulting hydrogen chloride salt of α-L-aspartyl-L-phenylalanine methyl ester is converted to α-L-aspartyl-L-phenylalanine methyl ester by neutralization.

The following examples are presented to more specifically illustrate the present invention but should not be considered as limiting the scope thereof.

EXAMPLE 1

Preparation of Formyl-α-L-aspartyl-L-phenylalanine

To 200 ml of water, 50% caustic solution is added to adjust the pH to 9.5. To the aqueous solution, L-phenylalanine (30 g, 0.181 mole) is dissolved while adding 11.8 ml of 50% caustic solution. After cooling the resultant solution to between −3° C. to +3° C., 14.5 ml of 50% caustic solution and formyl-L-aspartic anhydride (28.6 g, 0.199 mole) is added over a 1 hour period and the resulting reaction mixture is stirred for ½ hour at between −3° C. to 3° C. Upon lowering the pH of the mixture using 34.4 ml of hydrogen chloride, a solid precipitate is produced and it is separated by filtration. The precipitate is dried to obtain the desired formyl-α-L-aspartyl-L-phenylalanine (42.6 g, 0.138 mole). The remaining filtrate is collected and acidified to a pH of 6.0 with 9.4 ml of concentrated hydrogen chloride to produce the precipitate. The precipitate is filtered and dried to obtain additional formyl-α-L-aspartyl-L-phenylalanine (2.9 g, 0.009 mole). TLC analysis shows that there is no trace of β-isomer.

EXAMPLE 2

Preparation of α-L-aspartyl-L-phenylalanine 45.5 g of formyl-α-L-aspartyl-L-phenylalanine is dissolved in concentrated hydrogen chloride (18.2 ml) and water (141 ml). The mixture is treated at 60° C. for 4 hours to remove the formyl group. 11.7 g of 50% caustic solution is added into the resulting solution and cooled to 15° C. to obtain a precipitate of α-L-aspartyl-L-phenylalanine. After filtration, the precipitate is washed with 10 ml of water at 5° C. and dried to obtain 25.2 g (0.090 mole) of the desired product. The remaining filtrate is mixed with 50% caustic solution (6.5 g) and cooled to obtain the precipitate by filtration. The precipitate is washed with water (10 ml) at 5° C. and dried to obtain additional α-L-aspartyl-L-phenylalanine (12.2 g, 0.043 mole).

EXAMPLE 3

Preparation of α-L-aspartyl-L-phenylalanine methyl ester

The α-L-aspartyl-L-phenylalanine (20 g, 0.071 mole) is dissolved in the mixture of water (12.2 ml) and methanol (9.5 ml) and concentrated hydrogen chloride (26 ml) is added while stirring for 48 hours at room temperature to obtain as a precipitate the hydrogen chloride salt of α-L-aspartyl-L-phenylalanine methyl ester (20.3 g, 0.055 mole). After filtration, the cake of precipitate is dissolved in 355 ml of water. Then, the mixture is adjusted to a pH of 4.8 with 50% caustic solution (3.8 ml) and kept overnight at 5° C. to obtain a precipitate and separated by filtration. The filtered precipitate is washed with water (13 ml) at 5° C. and dried to obtain α-L-aspartyl-L-phenylalanine methyl ester (12.4 g, 0.042 mole).

EXAMPLE 4

Preparation of α-L-aspartyl-L-phenylalanine methyl ester

To the filtrate (30 ml) remaining after the filtration of the hydrogen chloride salt of α-L-aspartyl-L-phenylalanine methyl ester in the above Example 3, α-L-aspartyl-L-phenylalanine (6 g, 0.021 mole) is dissolved and methanol (1.0 ml) and concentrated hydrogen chloride (2.1 ml) is added. The resulting mixture is stirred for 48 hours to obtain as a precipitate the hydrogen chloride salt of α-L-aspartyl-L-phenylalanine methyl ester (6.4 g, 0.017 mole). After filtration, the precipitate is collected and dissolved in water (113 ml). Then, the mixture is adjusted to a pH of 4.8 with 50% caustic solution (1.2 ml) and kept overnight at 5° C. to obtain a precipitate. The filtered precipitate is washed with water (3.9 ml) at 5° C. and dried to obtain α-L-aspartyl-L-phenylalanine methyl ester (3.8 g, 0.013 mole).

EXAMPLE 5

Preparation of α-L-aspartyl-L-phenylalanine methyl ester

To the filtrate remaining after the filtration of hydrogen chloride salt of α-L-aspartyl-L-phenylalanine methyl ester in the above Example 4, α-L-aspartyl-L-phenylalanine (6 g, 0.021 mole) is dissolved, and methanol (1.0 ml) and concentrated hydrogen chloride (2.1 ml) is added. The resulting mixture is stirred for 48 hours to obtain as a precipitate the hydrogen chloride salt of α-L-aspartyl-L-phenylalanine methyl ester (6.6 g, 0.018 mole). After filtration, the precipitate is collected and dissolved in water (116 ml). Then, the mixture is adjusted to a pH of 4.8 with 50% caustic solution (1.2 ml) and kept overnight at 5° C. to obtain a precipitate. The filtered precipitate is washed with water (4.0 ml) at 5° C. and dried to obtain α-L-aspartyl-L-phenylalanine methyl ester (4.1 g, 0.014 mole).

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing an α-L-aspartyl-L-phenylalanine methyl ester of formula (I) by coupling a formyl-L-aspartic anhydride with a L-phenylalanine, which comprises the steps of:
   (a) reacting the formyl-L-aspartic anhydride of formula (II) with the L-phenylalanine in the presence of water at a pH 9–13 and at a temperature of from about −5° C. to 5° C., to produce a formyl-L-aspartyl-L-phenylalanine;
   (b) removing the formyl group from the formyl-L-aspartyl-L-phenylalanine and esterifying the resultant compound with methanol, hydrogen chloride and a filtrate which is obtained from a subsequent filtration step (d) to produce a hydrogen chloride salt of α-L-aspartyl-L-phenylalanine methyl ester;
   (c) neutralizing the hydrogen chloride salt of α-L-aspartyl-L-phenylalanine methyl ester; and
   (d) filtering the neutralized solution to produce the α-L-aspartyl-L-phenylalanine methyl ester;

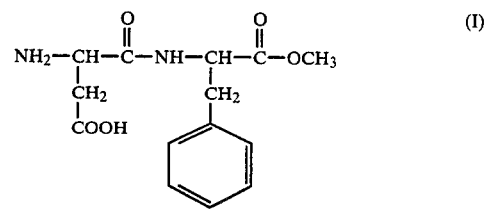

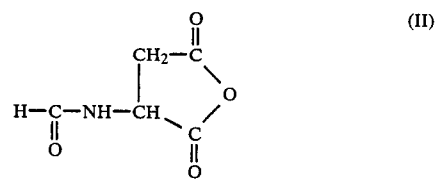

2. The process for preparing the α-L-aspartyl-L-phenylalanine methyl ester of claim 1 wherein the L-phenylalanine to be reacted is dissolved in water.

3. The process for preparing the α-L-aspartyl-L-phenylalanine methyl ester of claim 1 wherein the hydrogen chloride salt of α-L-aspartyl-L-phenylalanine methyl ester is prepared by the steps of deformylating the formyl-α-L-aspartyl-L-phenylalanine in the presence of hydrogen chloride, methanol and water, and adding methanol and hydrogen chloride directly to the resultant solution.

4. The process for preparing α-L-aspartyl-L-phenylalanine methyl ester of claim 1 wherein the hydrogen chloride salt of α-L-aspartyl-L-phenylalanine methyl ester is prepared by the steps of deformylating the formyl-α-L-aspartyl-L-phenylalanine in the presence of hydrogen chloride and water, separating the α-L-aspartyl-L-phenylalanine, and esterifying the α-L-aspartyl-L-phenylalanine in the presence of hydrogen chloride, water and methanol.

* * * * *